United States Patent [19]

Miller-Jones

[11] Patent Number: 4,576,045

[45] Date of Patent: Mar. 18, 1986

[54] WIDE APERTURE ULTRASONIC SCANNER EMPLOYING CONVEX TRANSDUCER ARRAY

[75] Inventor: Stockton M. Miller-Jones, Rancho Cordova, Calif.

[73] Assignee: General Electric Company, Milwaukee, Wis.

[21] Appl. No.: 566,865

[22] Filed: Dec. 29, 1983

[51] Int. Cl.⁴ .......................................... G01N 29/04
[52] U.S. Cl. ................................................... 73/626
[58] Field of Search ......................... 73/626; 367/105; 128/660

[56] References Cited

U.S. PATENT DOCUMENTS

| 4,208,916 | 6/1980 | Thomenius et al. | 73/626 |
| 4,344,327 | 8/1982 | Yoshikawa et al. | 73/626 |
| 4,409,982 | 10/1983 | Plesset et al. | 73/626 |
| 4,462,092 | 7/1984 | Kawabuchi et al. | 73/626 |
| 4,516,583 | 5/1985 | Richard | 73/626 |

Primary Examiner—Stewart J. Levy
Assistant Examiner—John E. Chapman, Jr.
Attorney, Agent, or Firm—Flehr, Hohbach, Test, Albritton & Herbert

[57] ABSTRACT

Disclosed is a wide aperture ultrasonic scanner which requires no moving parts. A convex array of transducer sub-elements is provided. Groups of sequential sub-elements form a transmission/reception element, and groups of transmission/reception elements are activated to form a vector. A plurality of vectors are defined by selectively removing and adding sequential sub-elements forming each element.

2 Claims, 5 Drawing Figures

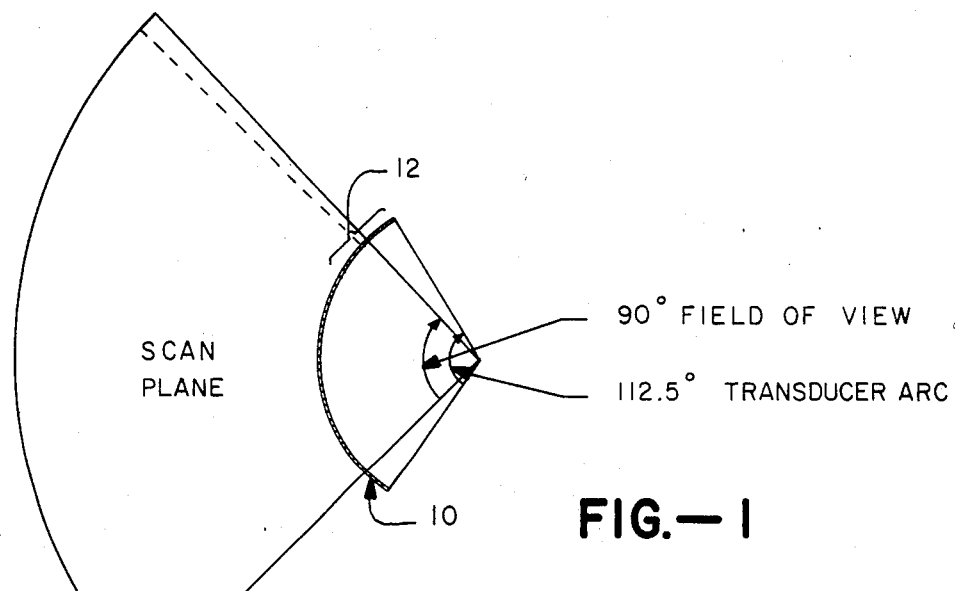
FIG.—1
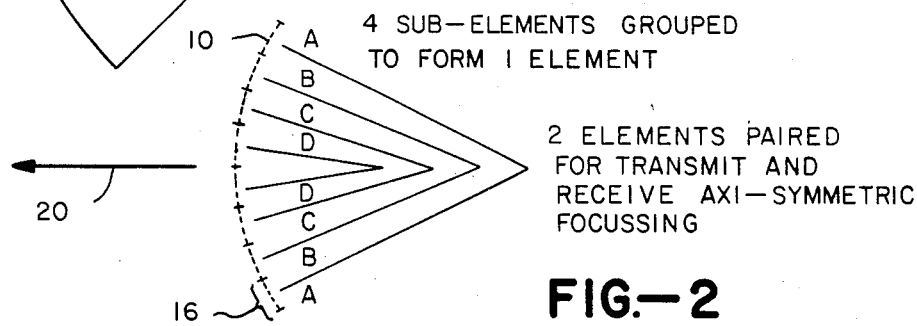
FIG.—2
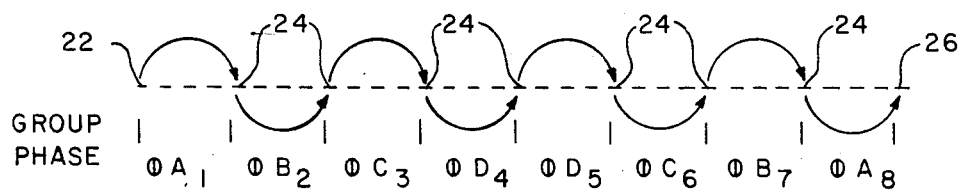
FIG.—3
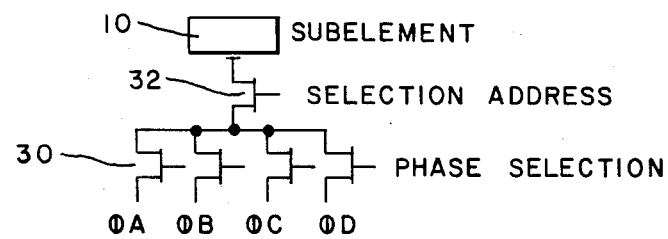
FIG.—4

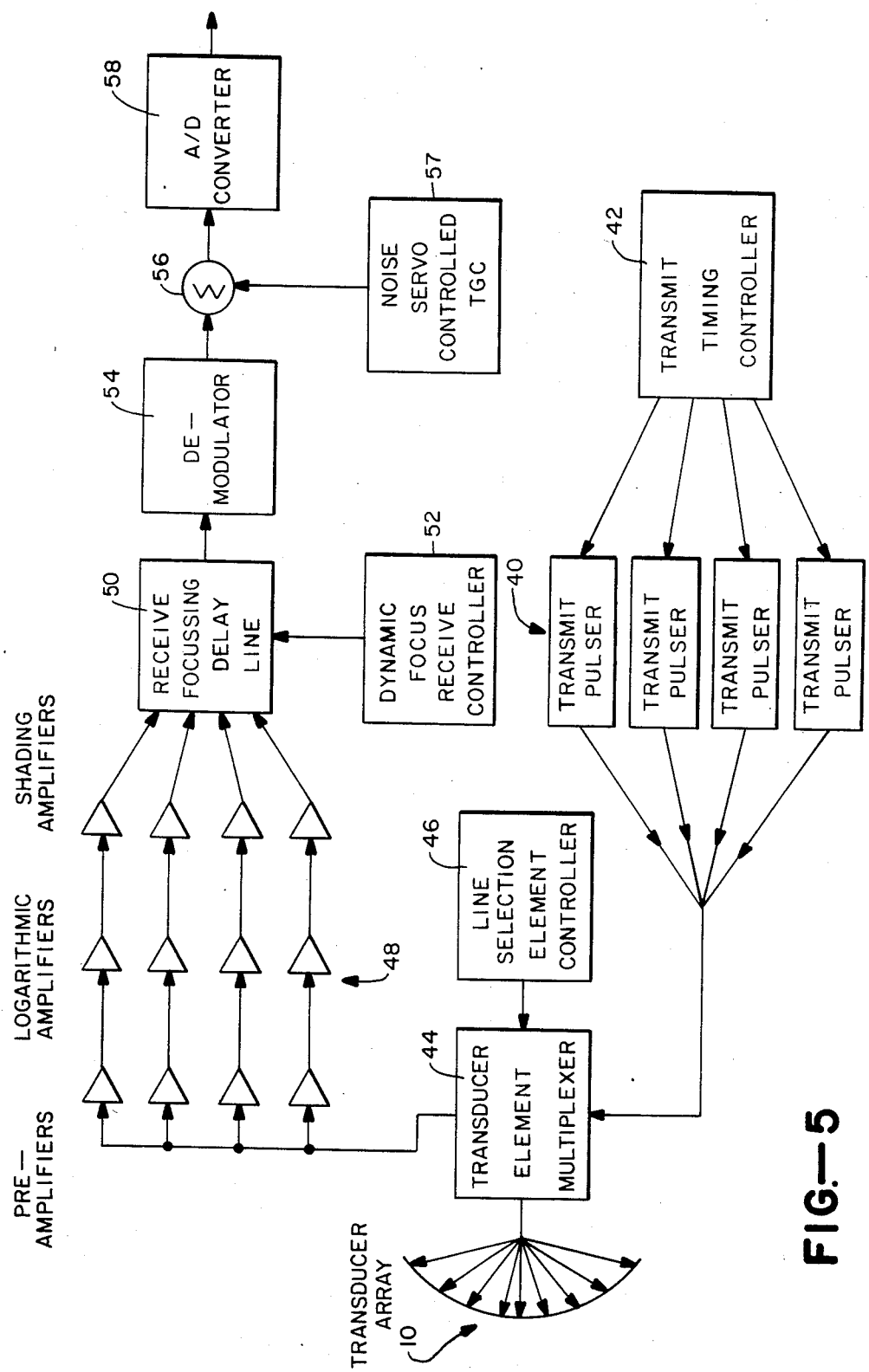
FIG.—5

WIDE APERTURE ULTRASONIC SCANNER EMPLOYING CONVEX TRANSDUCER ARRAY

This invention relates generally to ultrasonic scanners, and more particularly the invention relates to a wide aperture ultrasonic scanner.

Transducer scanners as used in medical ultrasonic imaging can project and receive focussed ultrasonic waves or project and receive ultrasonic waves in a wide field of view. Focussed transducers can include phased array linear transducer arrays and concave transducer arrays such as disclosed in U.S. Pat. No. 4,281,550. The wide aperture scanner typically employs a plurality of rotating transducers which are selectively energized to transmit a divergent ultrasonic beam. An example is the Datason Extended View Sector Module manufactured by General Electric Company and described in U.S. Pat. No. 4,402,223.

The present invention is directed to a wide aperture ultrasonic scanner which requires no moving parts. A convex array of transducer sub-elements is provided. Groups of sequential sub-elements form a transmission/reception element, and groups of transmission/reception elements are activated to form a vector. A plurality of vectors are defined by selectively removing and adding sequential sub-elements forming each element.

In a preferred embodiment 160 sub-elements are provided in an arc of 112.5°. Four sub-elements are grouped to form an element, and eight elements are grouped in forming a vector. The elements in a vector are phase activated to transmit and receive the vector. The sub-elements are incremented by one and re-grouped to form the next vector. A total of 128 vectors within an angle of 90° are provided from the 160 sub-elements spread over the 112.5° transducer arc.

Accordingly, an object of the present invention is an improved wide aperture ultrasonic scanner.

Another object of the invention is a wide aperture ultrasonic scanner having no moving parts.

The invention and objects and features thereof will be more readily apparent from the following detailed description and appended claims when taken with the drawing, in which:

FIG. 1 is a schematic view of a transducer array in accordance with one embodiment of the present invention.

FIG. 2 is a schematic diagram of elements of a vector using the array of FIG. 1.

FIG. 3 is a schematic representation of the incrementing of sub-elements in defining groups of vector elements in the array of FIG. 1.

FIG. 4 is a schematic diagram of control circuitry for each sub-element in the array of FIG. 1.

FIG. 5 is a functional block diagram of a scanning system using the ultrasonic scanner of FIG. 1.

Referring now to the drawing, FIG. 1 is a schematic view of a transducer array in accordance with one embodiment of the invention in which a plurality of transducer sub-elements shown generally at 10 are arranged in a convex array in a scan plane and are selectively grouped as shown at 12 and energized to define one of a plurality of vectors. In a preferred embodiment, 160 transducer sub-elements 10 are arranged in a convex array along an arc of 112.5°, and the sub-elements are grouped into a plurality of elements which are phase activated to define 128 vectors in a 90° field view. The radius of the array is determined by the transducer frequency and desired vector line density.

The transducer sub-elements may comprise conventional piezoelectric ceramic material formed, for example, by cutting an elongated bar of piezoelectric ceramic material mounted on a flexible support and then bending the flexible support in the desired arc. Each sub-element has a length on the order of one wavelength at the ultrasonic frequency. Four of the sub-elements are grouped to form an element, and eight elements are grouped to define one of the 128 vectors in the 90° field of view. To switch from one vector to the next, one sub-element is deleted, and another sub-element is added at either extreme of the selected aperture to provide the angular shift from one vector to the next.

FIG. 2 is a schematic diagram of a group of elements in the array of FIG. 1 for forming one vector. The vector is defined by 32 sub-elements with four sub-elements 10 grouped to form one of eight elements 16 for the vector 20. To define the vector 20 the eight elements 16 are phase activated in phases A, B, C, D as indicated. The outermost elements are activated by the first phase A, and the innermost elements are energized last by phase D, similar to the activation of a linear phased array of transducer elements.

FIG. 3 is a schematic diagram of the elements of FIG. 2 and illustrate the indexing of sub-elements in going from one vector to the next vector. Only one sub-element is added to the group of sub-elements and only one sub-element is deleted. In accordance with the multiplexing scheme of the invention, at the end of the line acquisition cycle only nine sub-elements need to be changed while the phase selection of other sub-elements is altered. Referring to FIG. 3, sub-element 22 is eliminated from the vector address, the phases of transducers 24 are adjusted, and sub-element 26 is added to the array when incrementing from one vector to the next vector.

The transducer switching scheme for accomplishing the multiplexing is shown in the schematic diagram of FIG. 4. Each transducer sub-element is controlled by a circuit illustrated in FIG. 4. A first plurality of switch devices such as field effect transistors shown generally at 30 are individually controlled by one of the phase signals $\phi_A$–$\phi_D$. The switches 30 are serially connected through a switch device 32 to the sub-element 10. Switch device 32 is controlled by the vector selection address. Thus, referring to FIG. 3 the vector selection address to the transistor 32 for the transducer sub-element 22 and 26 in FIG. 3 must be changed to delete and add sub-elements 22 and 26, respectively. The phase selection for the sub-elements 24 must be changed, and the switching circuitry for all other elements in FIG. 3 remains unchanged.

FIG. 5 is a functional block diagram of a scanning system using the curved array of FIG. 1. The basic architecture does not vary significantly from a conventional linear transducer array except for the array geometry. Suitable amplitude shading for sidelobe suppression must be provided. The shading function is also necessary to provide compensation of beam distortion caused by negative focal point due to the array geometry. To provide a focus in the scan plane, it is necessary to provide a compensatory amplitude weighting as well as phase delay schedule. The amplitude shading function that must be provided is a cosine weighting factor applied to each element being used to write one vector. That is, the center elements are amplified more heavily than the outer elements in a vector group according to a cosine functional schedule.

As shown in FIG. 5 four pulses are applied by pulsers 40, under control of transmit timing controller 42, to the transducer element multiplexer 44. The multiplexer 44, under control of the line selection element controller 46, then selectively energizes the transducer sub-elements 10 in the convex array to project waves along four vectors. The received signals for the four vectors are then applied through amplification and shading amplifiers shown generally at 48 and then through a focusing delay line 50 selectively controlled by controller 52. The delayed signals are then demodulated at 54 and then time gain amplified at 56 before conversion to digital form at 58.

The convex ultrasonic transducer array in accordance with the invention provides a wide field of view sector image format without requiring any moving parts. Only a portion of the transducer array is utilized to write a single vector with the portion being phase activated to define the direction of the selected image line. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:
1. A wide aperture ultrasonic scanner comprising
   a plurality of transducer sub-elements arranged in a convex array, each sub-element having a major surface for transmitting and receiving ultrasonic waves, said major surfaces being positioned outwardly in said convex array,
   means for activating adjacent sub-elements in a group as a plurality of phase activated elements to define a scan vector, each phase activated element comprising an equal number of adjacent sub-elements having the same phase, said means for activating said sub-elements including a plurality of switching circuits connected to said plurality of sub-elements, each switching circuit including a plurality of first switch means connected in parallel, each of said first switch means being controllable by a phase signal, and a second switch means connected in series with said plurality of first switch means and a sub-element, said second switch means being controllable by a vector address signal, and
   means for incrementing sub-elements in said group from one vector to the next vector by one sub-element to thereby define a plurality of vectors.
2. The wide aperture ultrasonic scanner as defined by claim 1 wherein each switch means comprises a field effect transistor.

* * * * *